US00PP29105P2

(12) United States Plant Patent
Butcher

(10) Patent No.: US PP29,105 P2
(45) Date of Patent: Mar. 13, 2018

(54) ***HIBISCUS* PLANT NAMED 'ROSINA'**

(50) Latin Name: *Hibiscus paramutabilis×syriacus*
Varietal Denomination: ROSINA

(71) Applicant: Polly Hill Arboretum, West Tisbury, MA (US)

(72) Inventor: Mary Louisa Butcher, West Tisbury, MA (US)

( * ) Notice: Subject to any disclaimer, the term of this patent is extended or adjusted under 35 U.S.C. 154(b) by 0 days.

(21) Appl. No.: 15/530,474

(22) Filed: Jan. 19, 2017

(51) Int. Cl.
*A01H 5/02* (2006.01)

(52) U.S. Cl.
USPC ..... Plt./257

(58) Field of Classification Search
USPC ..... Plt./257
CPC ..... A01H 5/02
See application file for complete search history.

*Primary Examiner* — Kent L Bell
(74) *Attorney, Agent, or Firm* — Cassandra Bright

(57) ABSTRACT

A new and distinct *Hibiscus* cultivar named 'ROSINA' is disclosed, characterized by clear light lavender single flowers without a distinctive dark eye. Plants are extremely dwarf and have lush dark green foliage. The new variety is a *Hibiscus*, normally produced as an outdoor garden or container plant.

2 Drawing Sheets

Figure 1:
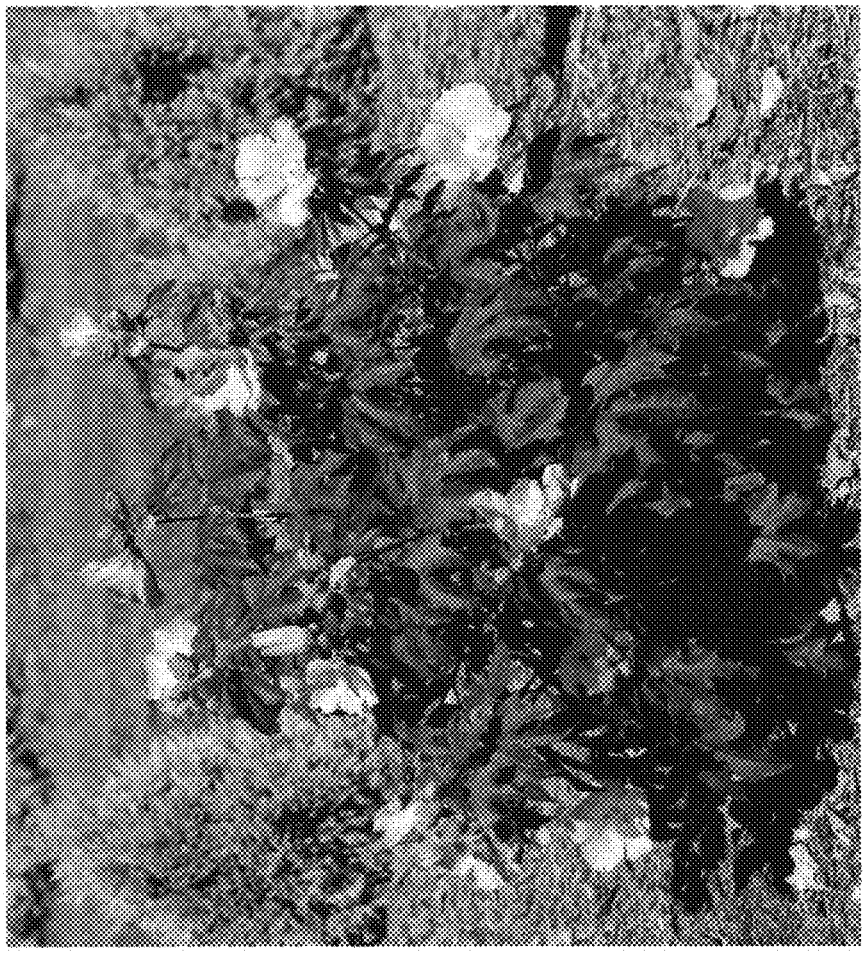

Latin name of the genus and species: *Hibiscus paramutabilis×syriacus*.

Variety denomination: 'ROSINA'.

BACKGROUND OF THE INVENTION

The new *Hibiscus* cultivar is a product of a planned breeding program conducted by the inventor, Mary Louisa Butcher Hill. The objective of the breeding program was to produce new *Hibiscus* varieties with dwarf plant habits. The open pollination resulting in this new variety was made during 1989 at a farm belonging to the inventor in West Tisbury, Mass.

The seed parent is not absolutely identified. Seed was collected from both *Hibiscus paramutabilis×syriacus* 'Tosca' and *Hibiscus paramutabilis×syriacus* 'Lohengrin'. Plants of both of these varieties were open pollinated. The pollen parent is also either *Hibiscus paramutabilis×syriacus* 'Tosca' or *Hibiscus paramutabilis×syriacus* 'Lohengrin'. The new variety was identified as a potentially interesting selection in August 1997. Selection was made at the same farm in West Tisbury, Mass.

Asexual reproduction of the new cultivar 'ROSINA' was first performed in July of 2007 at the farm in West Tisbury, Mass. by vegetative soft wood cuttings. Subsequent propagation has shown that the unique features of this cultivar are stable and reproduced true to type in multiple successive generations.

SUMMARY OF THE INVENTION

The cultivar 'ROSINA' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'ROSINA'

These characteristics in combination distinguish 'ROSINA' as a new and distinct *Hibiscus* cultivar:

1. Exceptionally dwarf plant.
2. Very dark, lush foliage.
3. Distinctive clear light lavender flowers without a distinctive dark center eye.

PARENT COMPARISON

Plants of the new cultivar 'ROSINA' are similar to plants of the variety *Hibiscus paramutabilis×syriacus* 'Tosca' in most horticultural characteristics, however, plants of the new cultivar 'ROSINA' differ in the following;

1. The new variety is significantly shorter, growing to 3 to 4 feet, compared to 10 to 12 feet.
2. The new variety produces smaller flowers.
3. Flowers of the new variety do not have the distinctive red eye seen in 'Tosca'.

Plants of the new cultivar 'ROSINA' are similar to plants *Hibiscus paramutabilis×syriacus* 'Lohengrin' in most horticultural characteristics, however, plants of the new cultivar 'ROSINA' differ in the following;

1. The new variety is significantly shorter, growing to 3 to 4 feet, compared to 10 to 12 feet.
2. The new variety produces smaller flowers.
3. Flowers of the new variety are solid lavender, flowers of 'Lohengrin' are white with a red eye.

COMMERCIAL COMPARISON

Plants of the new cultivar 'ROSINA' can be compared to the variety *Hibiscus* 'ILVO347', U.S. Plant Pat. No. 27,285. These varieties are similar in most horticultural characteristics however, 'ROSINA' differs in the following:

1. Flower color of the new variety is solid lavender. Flower color of this comparator is more pink and has a red center.

2. Plants of the new variety grow to approximately 3 to 4 feet, plants of this comparator grow to 8 to 12 feet.

BRIEF DESCRIPTION OF THE PHOTOGRAPHS

The accompanying photograph in FIG. 1 illustrates in full color a typical plant of 'ROSINA' grown in the ground outdoors in Grand Haven, Mich.

Figure 2:
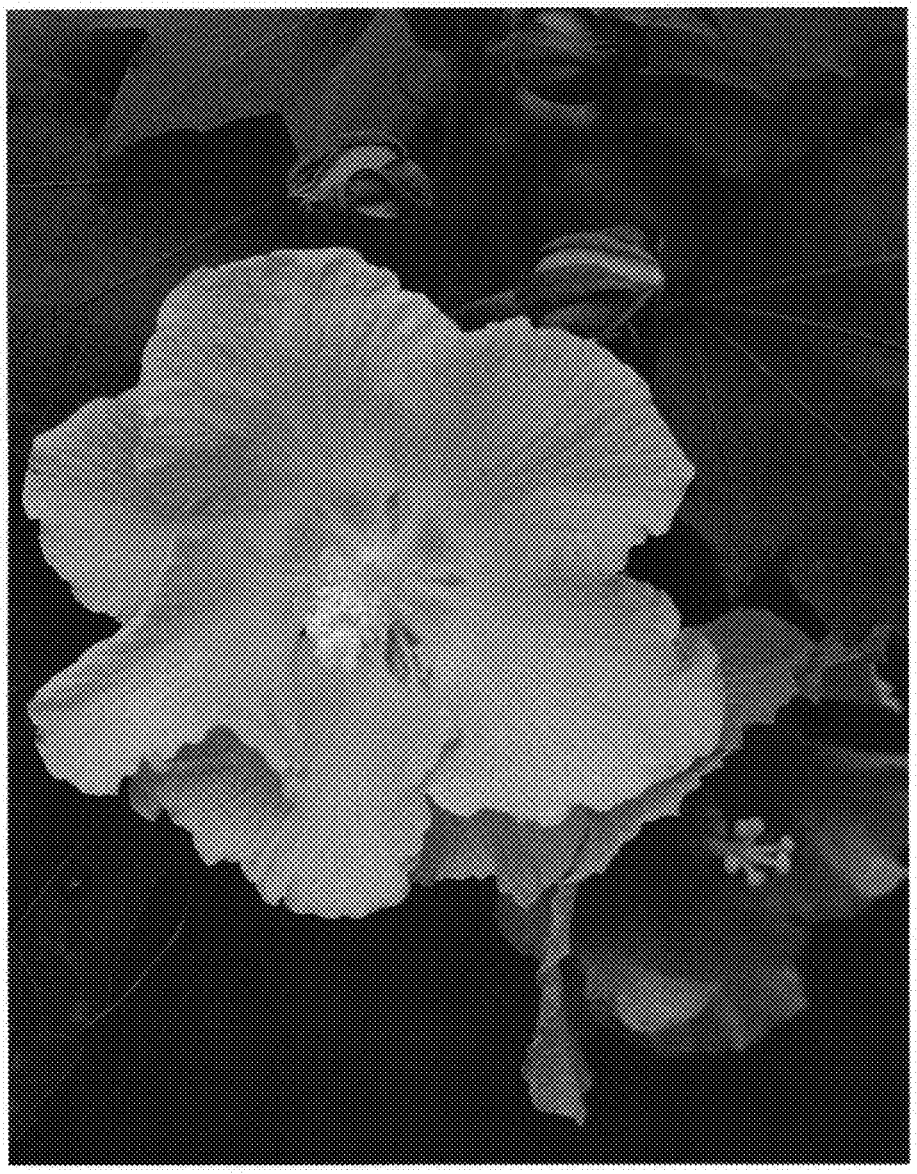

FIG. 2 illustrates in full color a typical flower of 'ROSINA'. Age of the plant photographed is approximately 2 years.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015, $6^{th}$ edition, except where general terms of ordinary dictionary significance are used. The following observations and measurements describe 'ROSINA' plants grown in a polyhouse in Grand Haven, Mich. Measurements were taken during the July of 2015. The plants were 2 years old in 3 gallon containers. The growing temperature ranged from approximately 18° C. to 27° C. during the day and 5° C. to 10° C. Measurements and numerical values represent averages of typical plant types.

Botanical classification: *Hibiscus paramutabilis*×*syriacus* 'ROSINA'.

PROPAGATION

Time to initiate roots: 20 days at approximately 25° C.

Root description: Fibrous, medium root thickness. Tan/brown in color, not effectively measured with a color chart.

Time to produce a rooted young plant: About 90 days at 25° C.

PLANT

Plant type: Perennial shrub.

Age of plant described: Approximately 2 years old.

Growth habit: Upright, globular.

Pot size of plant described: 3 gallon pot.

Height: 50 cm.

Plant spread: 73 cm.

Plant vigor: Strong dwarf plant.

Branching characteristics: Branching near base. Some pinching required to encourage a denser plant habit.

Length of primary lateral branches: 50 cm.

Diameter of lateral branches: 3 mm.

Quantity of lateral branches: Average 5.

Stem:

- *Stem shape.*—Round.
- *Stem strength.*—Sturdy and rigid.
- *Color.*—Stem: Near yellow-Green 145A, overlay Greyed-Green 194B. Bark: Near RHS Grey-Brown 199B with a hint of Yellow-Green 145A.
- *Texture.*—Woody with bark.
- *Angle of attachment.*—Average angle 30 to 45° from center of plant.

Internode length: 5.3 cm on average.

FOLIAGE

Leaf:

- *Arrangement.*—Single leaves, 3 to 4 protruding from same node on same side of stem.
- *Leaf shape.*—Hastate.
- *Average length.*—10 to 12 cm.
- *Average width.*—8 cm.
- *Apex.*—Acuminate.
- *Base.*—Cuneate.
- *Margin.*—Lobed and coarsely crenate.
- *Texture of top surface.*—Smooth and slightly scabrose.
- *Texture of bottom surface.*—Smooth and slightly scabrose with distinct veins.
- *Color.*—Young foliage upper side: Near RHS Green 141A. Young foliage under side: Near RHS Yellow-Green 146B. Mature foliage upper side: Near RHS Green 139A. Mature foliage under side: Near RHS Yellow-Green 147B.
- *Venation.*—Pattern: Palmate. Venation coloration: Prominent feature in leaf blade. Color upper side: Near RHS Yellow-Green 145A. Color under side: Near RHS Yellow-Green 145C.
- *Petiole.*—Average Length: 3 to 7 cm. Diameter: 3 mm. Petiole color upper side: Near RHS Green 137B over a hint of Yellow-Green 145A. Petiole color lower side: Near RHS Green 137C over a hint of 145B. Petiole Texture upper side: Slightly pubescent. Petiole Texture lower side: Smooth.
- *Stipules.*—2 stipules on either side of leaf grouping. 8 mm long, less than 1 mm wide, colored near Grey-Brown 199D.

FLOWER

Natural flowering season: Late Spring through Late Summer.

Flowering form: Single, rotate.

Flower habit: Solitary, emerging from leaf axils.

Flower longevity on plant: About 2 to 3 days.

Quantity of flowers per plant: About 50 flowers and buds on a mature plant in full bloom.

Flower aspect: Upright and outward.

Size:

- *Length.*—8 to 9 cm.
- *Diameter.*—6 to 11 cm.

Flower other characteristics:

- *Persistence.*—Self-cleaning.
- *Fragrance.*—Subtle floral scent.

Bud:

- *Shape.*—Oval.
- *Length.*—Average 2.0 to 4.0 cm, depending on maturity.
- *Diameter.*—Average 1.0 to 2.0 cm, depending on maturity.
- *Color.*—Near Purple 75A, striations of White 155D.

Petal:

- *Petal arrangement.*—Single overlapping whorl.
- *Number of petals per flower.*—5.
- *Fused.*—No.
- *Petal shape.*—Obovate.
- *Petal base.*—Attenuate.
- *Margin.*—Undulate.
- *Tip shape.*—Obutuse.

*Length.*—5.0 cm.
*Width.*—4.0 cm.
*Texture.*—Upper: Glabrous, soft. Lower: Glabrous, soft.
*Appearance.*—Delicate, with slightly matte appearance upper and lower surfaces.

Petal color:
*When opening.*—Upper surface: Base of Purple Group 75B, with shading of Purple-Violet Group 82B into Violet Blue 90A. Lower surface: Base of Purple 75C, with shading of Purple-Violet Group 82C into Violet-Blue 90B.
*Fully opened.*—Upper surface: Base of Purple Group 75A with shading into Violet-Blue Group 89C. Lower surface: Base of Purple Group 75A with shading into Violet-Blue Group 89C.
*Fading to.*—Upper surface: Base of Purple Group 75A fading to Violet-Blue Group 89C. Lower surface: Base of Purple Group 75A with fading to Violet-Blue Group 89C.

Sepal:
*Arrangement.*—Radial.
*Number.*—Average 5 or 6.
*Shape.*—Narrow deltate.
*Tip.*—Narrowly acute.
*Base.*—Truncate.
*Margin.*—Entire.
*Length.*—3.5 cm.
*Width.*—2 mm.
*Texture, upper.*—Glabrous.
*Texture, lower.*—Glabrous.
*Color.*—Mature: Upper surface: Near Green 139B. Under surface Near Green 139B.

Calyx:
*Shape.*—Funnelform.
*Length.*—2.5 cm.
*Diameter.*—1.5 cm.

Peduncle:
*Length.*—5 cm.
*Diameter.*—3 mm.
*Color.*—Near RHS Yellow-Green 146B.
*Orientation.*—25°.
*Strength.*—Rigid.
*Texture.*—Slightly pubescent.

REPRODUCTIVE ORGANS

Stamens:
*Number.*—Average 48, clustered and implanted in style, typical of *Hibiscus.*
*Filament length.*—6 mm.
*Filament color.*—Near RHS White 155A.

Anthers:
*Shape.*—Narrow globular.
*Length.*—2 mm.
*Color.*—Near RHS White 155A.
*Pollen color.*—Near RHS White 155A.
*Pollen amount.*—Moderate.

Pistil:
*Number.*—1.
*Length.*—4.25 cm.
*Style.*—Length: 3.7 cm. Color: Near RHS White 155C.
*Stigma.*—Shape: Peltate. Color: Near RHS White 155A.
*Ovary color.*—Near RHS White 155C with light shading of Red-Purple 60B.

OTHER CHARACTERISTICS

Seeds and fruits: Not observed to date.
Disease/pest resistance: Neither resistance nor susceptibility to normal diseases and pests of *Hibiscus paramutabilis*× *syriacus* have been observed.
Garden performance: Good tolerance for wind and rainy conditions.
Temperature tolerance: Low temperature tolerance to −26° C., high temperature tolerance to 35° C.

What is claimed is:

1. A new and distinct cultivar of *Hibiscus* plant named 'ROSINA' as herein illustrated and described.

* * * * *